US 12,114,989 B2

United States Patent
Assaf et al.

(10) Patent No.: US 12,114,989 B2
(45) Date of Patent: Oct. 15, 2024

(54) APPARATUS AND METHOD FOR UTILIZING A BRAIN FEATURE ACTIVITY MAP DATABASE TO CHARACTERIZE CONTENT

(71) Applicant: Brainvivo Ltd., Tel Aviv (IL)

(72) Inventors: Yaniv Assaf, Tel Aviv (IL); Assaf Horowitz, Tel Aviv (IL)

(73) Assignee: BRAINVIVO LTD., Tel Aviv (IL)

( * ) Notice: Subject to any disclaimer, the term of this patent is extended or adjusted under 35 U.S.C. 154(b) by 1034 days.

(21) Appl. No.: 16/667,198

(22) Filed: Oct. 29, 2019

(65) Prior Publication Data

US 2020/0170524 A1 Jun. 4, 2020

Related U.S. Application Data

(60) Provisional application No. 62/775,018, filed on Dec. 4, 2018.

(51) Int. Cl.
*A61B 5/00* (2006.01)
*A61B 5/16* (2006.01)
(Continued)

(52) U.S. Cl.
CPC .............. *A61B 5/4064* (2013.01); *A61B 5/16* (2013.01); *A61B 5/24* (2021.01); *A61B 5/7246* (2013.01);
(Continued)

(58) Field of Classification Search
CPC ........... A61B 5/24; A61B 5/16; A61B 5/4064; A61B 5/7246; A61B 5/7264; A61B 5/055;
(Continued)

(56) References Cited

U.S. PATENT DOCUMENTS 4,583,190 A * 4/1986 Salb .................. A61B 5/374
  708/404
7,643,863 B2 1/2010 Basser et al.
(Continued)

FOREIGN PATENT DOCUMENTS

CN 102855352 A 1/2013
CN 106691378 A 5/2017
(Continued)

OTHER PUBLICATIONS

International Search Report and Written Opinion mailed Feb. 27, 2020 for PCT Application No. PCT/IB2019/060414. 8 pages.
(Continued)

*Primary Examiner* — Yi-Shan Yang
*Assistant Examiner* — Joseph A Tombers
(74) *Attorney, Agent, or Firm* — MEITAR PATENTS LTD.

(57) ABSTRACT

A computer implemented method includes supplying stimuli to an organism, measuring brain activity of the organism responsive to the stimuli and producing a brain feature activity map characterizing the brain activity. The operations of supplying, measuring and producing are repeated for different stimuli to form a brain feature activity map database. New stimuli are received. New stimuli features are mapped to a projected brain activity map. The projected brain activity map is compared to the brain feature activity map database to identify similarities and dissimilarities between the projected brain activity map and entries in the brain feature activity map database to designate a match. The new stimuli are characterized based upon the match.

15 Claims, 3 Drawing Sheets

(51) Int. Cl.
  *A61B 5/24* (2021.01)
  *G01N 29/44* (2006.01)
  *G06F 18/22* (2023.01)
  *G06V 30/413* (2022.01)
  *G16H 30/00* (2018.01)
  *G16H 50/50* (2018.01)

(52) U.S. Cl.
  CPC ....... *A61B 5/7264* (2013.01); *G01N 29/4409* (2013.01); *G01N 29/4472* (2013.01); *G06F 18/22* (2023.01); *G06V 30/413* (2022.01); *G16H 30/00* (2018.01); *G16H 50/50* (2018.01); *G06F 2218/00* (2023.01); *G06T 2207/10072* (2013.01); *G06T 2207/10088* (2013.01); *G06T 2207/30* (2013.01); *G06T 2207/30016* (2013.01)

(58) Field of Classification Search
  CPC ......... A61B 5/245; A61B 5/291; A61B 5/372; A61B 5/377; G01N 29/4409; G01N 29/4472; G06K 9/00496; G06K 9/6215; G06V 30/413; G16H 30/00; G16H 50/50; G06T 2207/10072; G06T 2207/10088; G06T 2207/30; G06T 2207/30016; G01R 33/4806
  See application file for complete search history.

(56) References Cited

U.S. PATENT DOCUMENTS

| | | | |
|---|---|---|---|
| 9,788,753 | B2 | 10/2017 | Assaf et al. |
| 2008/0004660 | A1 | 1/2008 | Assaf et al. |
| 2008/0097235 | A1 | 4/2008 | Ofek et al. |
| 2010/0069777 | A1* | 3/2010 | Marks ............... A61B 5/16 600/544 |
| 2010/0249573 | A1 | 9/2010 | Marks |
| 2015/0012111 | A1 | 1/2015 | Contreras-Vidal et al. |
| 2015/0248470 | A1 | 9/2015 | Coleman et al. |
| 2015/0248615 | A1 | 9/2015 | Parra et al. |
| 2016/0019693 | A1* | 1/2016 | Silbersweig ......... G06T 11/60 382/128 |
| 2016/0054409 | A1 | 2/2016 | Wager et al. |
| 2016/0103487 | A1* | 4/2016 | Crawford ........... A61B 5/117 600/544 |
| 2016/0128620 | A1 | 5/2016 | Iriki et al. |
| 2016/0284082 | A1* | 9/2016 | Varkuti ............ A61B 5/055 |
| 2016/0346164 | A1 | 12/2016 | Ward et al. |
| 2018/0240221 | A1* | 8/2018 | Rijnders ........... G06V 10/431 |
| 2019/0083805 | A1* | 3/2019 | Etkin .............. A61B 5/0261 |
| 2019/0156352 | A1 | 5/2019 | Pradeep et al. |
| 2019/0159712 | A1 | 5/2019 | Marks |
| 2019/0246936 | A1 | 8/2019 | Garten et al. |
| 2019/0287238 | A1 | 9/2019 | Sriraman |
| 2020/0005339 | A1 | 1/2020 | Pradeep et al. |
| 2020/0008725 | A1 | 1/2020 | Bach et al. |
| 2020/0193299 | A1 | 6/2020 | Geva et al. |
| 2020/0286505 | A1 | 9/2020 | Osborne et al. |

FOREIGN PATENT DOCUMENTS

| | | |
|---|---|---|
| JP | 2004194924 A | 7/2004 |
| JP | 2016101479 A | 6/2016 |
| JP | 2016212772 A | 12/2016 |
| WO | 2011093557 A1 | 8/2011 |
| WO | 2012101644 A2 | 8/2012 |
| WO | 2016110804 A1 | 7/2016 |
| WO | 2016132228 A2 | 8/2016 |
| WO | 2017085168 A1 | 5/2017 |
| WO | 2020095131 A1 | 5/2020 |

OTHER PUBLICATIONS

AU Application # 2019391425 Office Action dated Oct. 22, 2021.
International Application # PCT/IB2021/062329 Search Report dated Apr. 10, 2022.
Han et al., "Learning Computational Models of Video Memorability from fMRI Brain Imaging," IEEE Transactions on Cybernetics, vol. 45, No. 8, pp. 1692-1703, Aug. 2015.
EP Application # 19894376.3 Search Report Jul. 22, 2022.
JP Application # 2021530305 Office Action dated Jan. 10, 2023.
U.S. Appl. No. 17/148,607 Office Action dated Mar. 21, 2023.
JP Application # 2021530305 Office Action dated Jun. 13, 2023.
International Application # PCT/IB2023/054156 Search Report dated Aug. 13, 2023.
U.S. Appl. No. 17/148,607 Office Action dated Aug. 29, 2023.
CN Application # 2019800785972 Office Action dated Nov. 28, 2023.
KR Application # 1020217018841 Office Action dated Mar. 19, 2024.
CN Application # 2019800785972 Office Action dated May 9, 2024.
U.S. Appl. No. 17/148,607 Office Action dated Apr. 9, 2024.
EP Application # 21919231.7 Search Report dated Jul. 19, 2024.

\* cited by examiner

APPARATUS AND METHOD FOR UTILIZING A BRAIN FEATURE ACTIVITY MAP DATABASE TO CHARACTERIZE CONTENT

CROSS-REFERENCE TO RELATED APPLICATION

This application claims priority to U.S. Provisional Patent Application Ser. No. 62/775,018, filed Dec. 4, 2018, the contents of which are incorporated herein by reference.

FIELD OF THE INVENTION

This invention relates generally to an automated evaluation of content to determine a cognitive classification. More particularly, this invention is directed toward techniques for utilizing a brain feature activity map database to characterize content.

BACKGROUND OF THE INVENTION

Machine Learning and Deep Learning are branches of the field of Artificial Intelligence that are based on the idea that computational systems can learn from data. The human brain was always a source of inspiration to these methods, especially for the learning processes of the computational systems. The human brain and its underlying biological neural networks have an efficient way to process a small amount of data to promptly reach a cognitive classification.

Individuals posting objectionable content, such as violent, sexual, abusive or offensive content, compromises user social media experiences. Social media providers endeavor to remove such content, but existing techniques are manual and are therefore slow and cumbersome. Accordingly, there is a need for automated evaluation of content to determine a cognitive classification (e.g., objectionable versus non-objectionable, fake versus real, pleasant versus unpleasant, etc.).

SUMMARY OF THE INVENTION

A computer implemented method includes supplying stimuli to an organism, measuring brain activity of the organism responsive to the stimuli and producing a brain feature activity map characterizing the brain activity. The operations of supplying, measuring and producing are repeated for different stimuli to form a brain feature activity map database. New stimuli are received. New stimuli features are mapped to a projected brain activity map. The projected brain activity map is compared to the brain feature activity map database to identify similarities and dissimilarities between the projected brain activity map and entries in the brain feature activity map database to designate a match. The new stimuli are characterized based upon the match to establish a cognitive classification.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1:
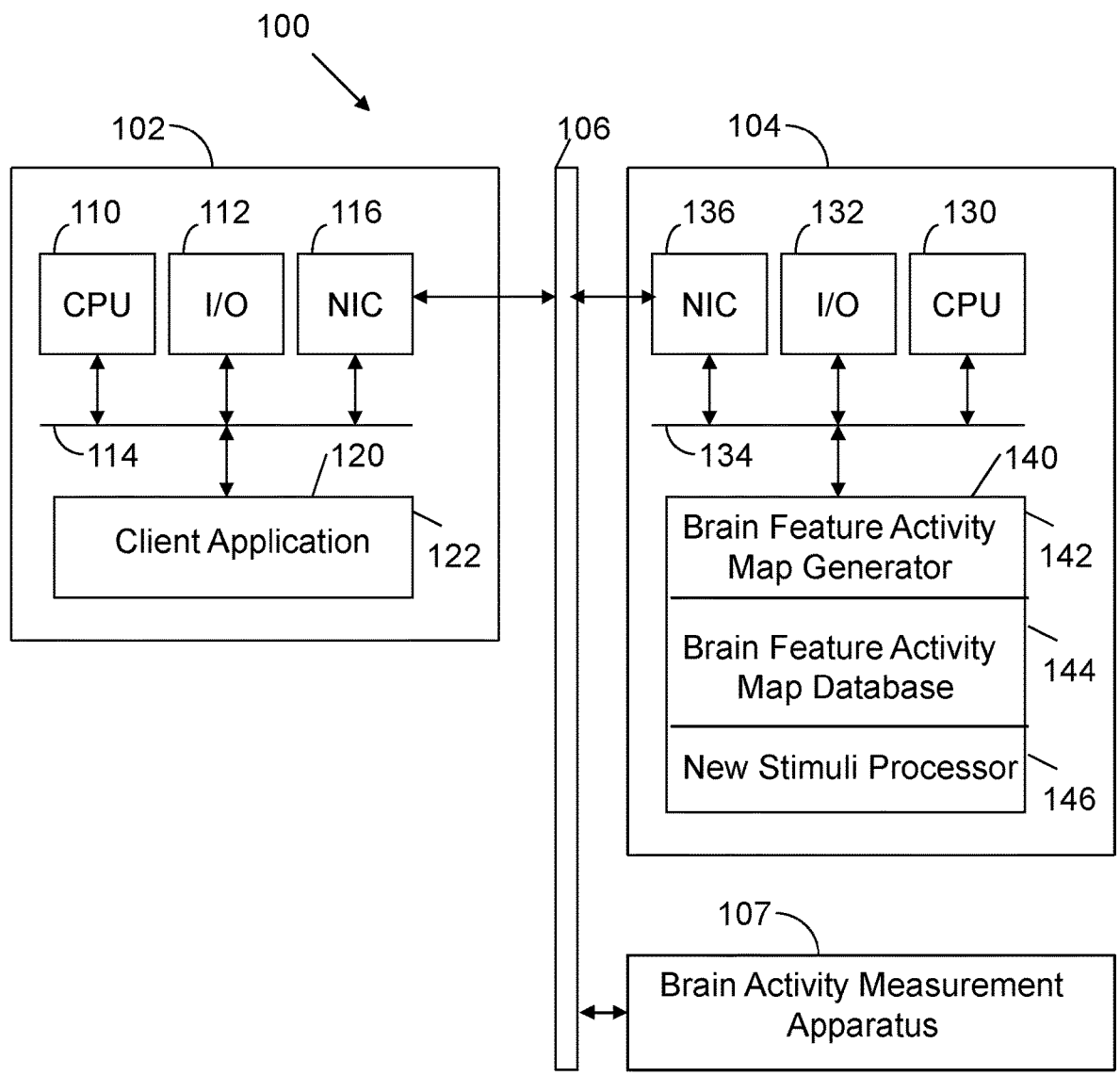
FIG. 1 illustrates a system configured in accordance with an embodiment of the invention.

FIG. 1 illustrates a system 100 with a client device 102 in communication with a server 104 via a network 106, which may be any combination of wired and wireless networks. A brain activity measurement apparatus 107, such as a Magnetic Resonance Imaging (MRI) apparatus is also connected to network 106. As discussed in detail below, the brain activity measurement apparatus 107 is used to generate brain feature activity maps for different stimuli supplied to an organism, such as a human. The brain feature activity map is generated by projecting measurable brain signals from the brain response to given stimuli to an anatomical atlas of the brain (e.g., Brodmann map, AAL map, etc.,). In this process, the given stimuli are broken down into a set of predefined features, where a correlation between each feature to brain activity is tested through similarity analysis. The brain feature activity maps are then used to generate a brain feature activity map database, which is used to categorized new stimuli according to its content (e.g., violent, sexual, offensive, abusive, positive, negative, neutral, etc.,) and a decision making process regarding its objectionable or non-objectionable nature. Thus, the system provides an automated technique for categorizing and characterizing new content.

The new content may be submitted to the server 104 from the client device 102. The new content may be an image, video, audio or sensory content. The client device 102 may be a computer, tablet, smartphone and the like. The client device 102 includes a central processing unit 110 connected to input/output devices 112 via a bus 114. The input/output devices 112 may include a keyboard, mouse, touch display and the like. A network interface circuit 116 is also connected to the bus 114 to provide connectivity to network 106. A memory 120 is also connected to bus 114. The memory 120 stores a client application 122, which may be used to interact with server 104. Client device 102 and server 104 may be cloud-based resources operating automatically without user input.

Server 104 includes a central processing unit 130, input/output devices 132, a bus 134 and a network interface circuit 136. A memory 140 is connected to bus 134. The memory 140 stores instructions executed by processor 130 to implement operations disclosed herein. The memory 140 stores a brain feature activity map generator 142, which includes instructions to produce a brain feature activity map characterizing brain activity responsive to stimuli presented to an organism. Different stimuli and different subjects are used to collect brain feature activity maps to form a brain feature activity map database 144. The memory 140 also stores a new stimuli processor 146. The server 104 receives new stimuli, such as from client device 102, and maps features of the new stimuli to a projected brain activity map. The projected brain activity map is an estimation of the brain response to new stimuli. The estimation is made by extracting pre-defined features of the new stimuli, finding a match for the closest set of features from the brain feature activity map (through similarity analysis) and calculating the brain response to the new stimuli by combining the relevant brain feature activity from all features.

During the creation of the projected brain activity map, the labeling of the brain feature activity map is also being estimated. The generation of the new stimuli label is made by a set of predictors. The latter predicts the similarities and dissimilarities between each feature to the labeling of the corresponding brain response from the brain feature activity map database 144. The new stimuli are characterized based upon the match or a combination of designated matches.

Figure 2:
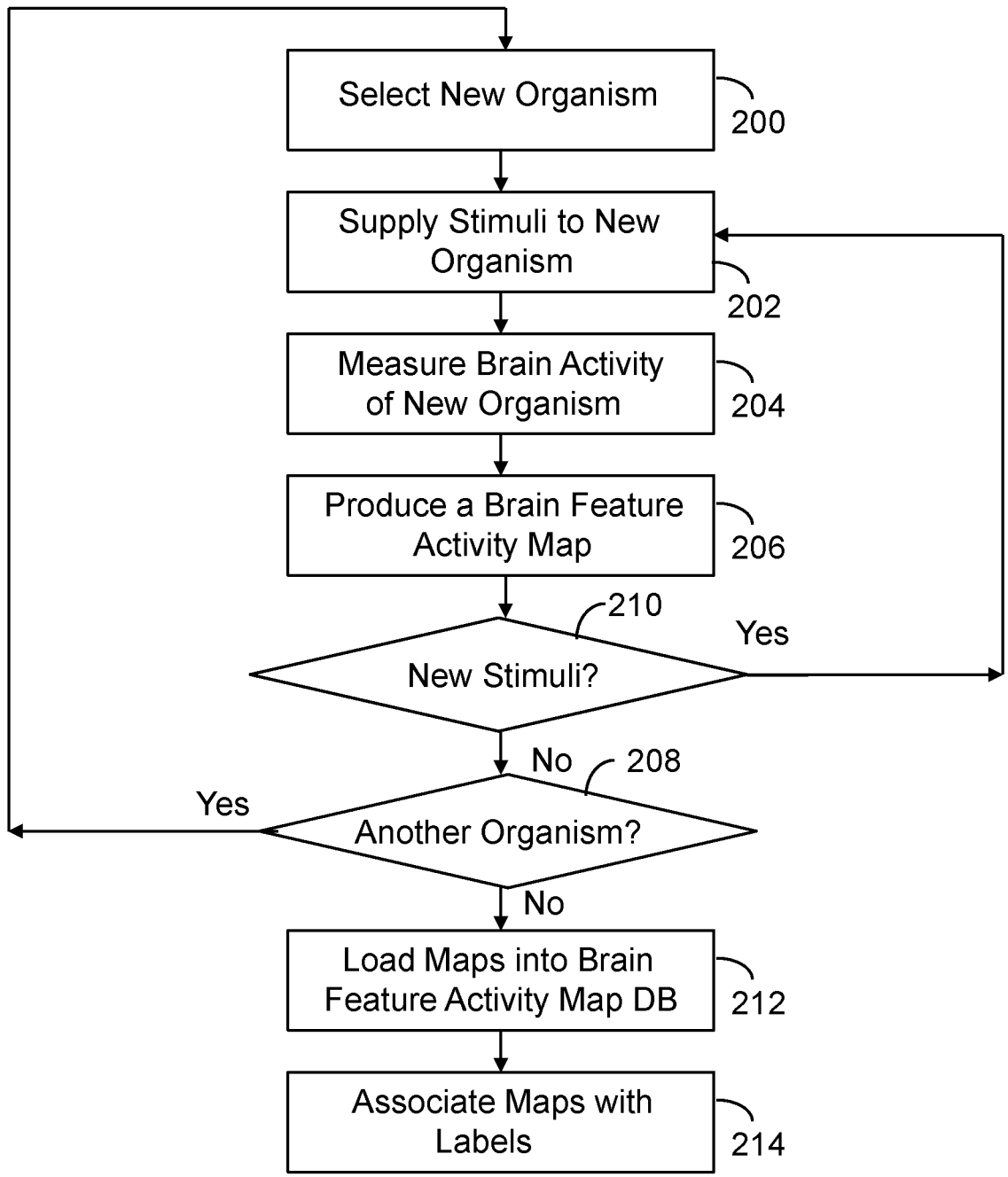
FIG. 2 illustrates processing operations to construct a brain feature activity map database in accordance with an embodiment of the invention.

FIG. 2 illustrates processing operations to construct the brain feature activity map database 144. Initially, an organism is selected 200. Typically, the organism is a human, but other life forms may be used in accordance with embodiments of the invention. The organism is connected to a brain activity measurement apparatus 107. Stimuli are then supplied to the new organism 202. The brain activity of the new organism responsive to the stimuli is measured 204. Typically, the measure is in the form of an image, which is then transformed into a brain feature activity map, as detailed below. The same organism may then be exposed to new stimuli (210—Yes), in which case operations 202-206 are performed again. If the subject is not to be presented with new stimuli (210—No), it is determined whether another organism is to be tested 208. If so (208—Yes), operations 200-210 are repeated. Thus, the process potentially constructs multiple brain feature activity maps for multiple organisms for multiple stimuli. When no other organism is to be evaluated (208—No), the brain feature activity maps are loaded into a brain feature activity database 212. The brain feature activity maps may then be associated with labels 214, as described in detail below.

Figure 3:
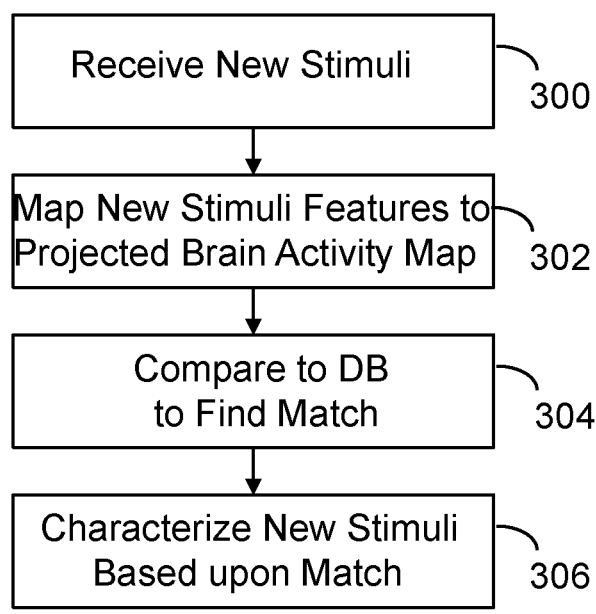
FIG. 3 illustrates processing operations to utilize a brain feature activity map database to characterize content.

Once the brain feature activity map database 144 is constructed, it may be used to characterize new stimuli. In particular, new stimuli processor 146 may be used to receive new stimuli from client machine 102. Alternately, the new stimuli processor 146 may be implemented on the client machine 102. FIG. 3 shows an initial operation to receive new stimuli 300. New stimuli features are mapped to a projected brain activity map 302. This operation is consistent with the operation to produce a brain feature activity map 206 of FIG. 2. The projected brain activity map is compared to the brain activity map database 144 to find a match 304. The new stimuli are characterized based upon the match 306. In other words, labels associated with the match are associated with the new stimuli.

The brain feature activity map utilizes a transformation that relates non-specific image features to a pattern, or a non-specific series of video frames to a series of patterns, of brain activity using a functional encoding approach. Measurements are performed by one or more of Anatomical Magnetic Resonance Imaging (MRI), Diffusion MRI (dMRI), Functional MRI (fMRI), Electroencephalogram (EEG), Magnetoencephalogram (MEG), Infrared Imaging, Ultraviolet Imaging, Computed Tomography (CT), Brain Mapping Ultrasound, In-Vivo Cellular Data, In-Vivo Molecular data, genomic data, and optical imaging. The brain activity includes a brain signal (such as bold signals from fMRI, ERP signals from EEG, etc.) in predefined brain regions.

The brain feature activity model integrates anatomical, connectivity and activity analyses. The activity signal in this method is analyzed to extract stimuli feature-dependent regional brain response. The brain activity response is de-correlated using a connectivity matrix between the same regions to increase variability between features.

In one embodiment, an image from the brain activity measurement apparatus 107 is evaluated to determine how the activity of brain signals (such as BOLD signal from fMRI, ERP signals from EEG, etc.,) in predefined brain regions (see definition in the next section) can explain the selected cognitive layers. The Brain activity recording analysis may be, for example, how the BOLD signal of fMRI can explain the presence of a face in an image. Such an approach (similar to Galant lab publications of encoding-decoding using fMRI) can provide whole-brain holistic representations of different cognitive layers. The cognitive layers are then multiplied by a connectivity association matrix to form a feature specific brain association matrix, referred to as a Brain Connectome.

Brain Connectome is computed either functionally (resting-state fMRI), structurally (diffusion-based fiber tracking), or a combination of the two, and may be weighted by various micro-structure estimates of the tissue (e.g., number of streamlines, axon diameter distribution, etc).

Each of the stimuli undergoes decomposition into features and feature sets. These features may represent image content in reciprocal space, such as a Fourier transform of an image feature. The entire set of event-related measurements undergo analysis through modeling, such as a general linear model or other approaches to representing regional feature-specific brain activity.

Using the brain feature activity map database, in a reverse engineering approach, new stimuli is deconstructed into its feature space and is then modeled (through a GLM or example) to create the image specific brain response regional code. This simulation or modeling provides a regional brain response as if the perception of the image was measured via a brain activity measurement apparatus.

In one embodiment, gray matter architecture, white matter architecture and dynamic functions of diverse networks and sub-networks in the brain are collected. The gray matter data is converted into normalized, regional gray matter indices ("Brain Regions"). Analyzed white matter data is converted into weighted neuronal connections ("Brain Connectome"). Brain functional and physiological data is augmented with the Brain Regions and then weighted according to the Brain Connectome, thereby creating an additional weighted map of brain activity. The brain activity map labels each brain region according to its stimuli-specific activity ("Activity Labels"). The Activity Labels are a continuous numeric index that represents the intensity of brain activity within each Brain Region, while taking into consideration the interaction between the Brain Regions (i.e., weighted according to the Connectome).

The Brain Regions are calculated from the brain gray matter anatomical data (e.g., Anatomical Magnetic Resonance Imaging (MRI), Diffusion Tensor Imaging (DTI), as well as other in-vivo imaging technologies of the gray matter) and are averaged over a segmented brain atlas. The Brain Connectome is calculated from the brain white matter anatomical data (e.g., Anatomical Magnetic Resonance Imaging (MRI), Diffusion Tensor Imaging (DTI), Infrared Imaging, as well as other in-vivo imaging technologies of the white matter of the brain). White matter indices are based on micro-structure estimation of brain tissue (e.g., mean diffusivity, fractional anisotropy, radial diffusivity, axonal density, axonal diameter, axonal conduction velocity, etc.,) and are used to characterize the Brain Connectome on its micro-structural level. The characterization of the Brain Connectome by these features creates a matrix that contains the biological weights between Brain Regions. For example, a large number of axons (a micro-structural feature of the brain tissue) that connect two brain regions, demonstrates a strong degree of connectivity between these two hubs in the network (i.e., the higher the number of axons, the stronger the connection is). Using neuroimaging techniques to reveal the micro-structural properties of the white matter yields Brain Connectome that reveals the underlying connectivity of the brain network.

The Activity Labels are calculated from brain functional and physiological imaging (e.g., Diffusion Tensor Imaging (DTI), Functional MIR (fMRI), Electroencephalogram (EEG), as well as other physiological and functional in-vivo imaging technologies of the brain) to identify the stimuli-specific activity of each brain region. The Activity Labels are created when the stimuli are introduced to an organism while conducting the brain functional and physiological imaging. During this phase, the organism is required to complete a labeling task when perceiving the stimuli. The stimuli can be any data that can be perceived by the organism senses (e.g., visual, audio, tactile, odor and taste). The process of presenting the stimuli includes an apparatus to deliver the stimuli, according to its nature (e.g., a screen, speaker, tactile stimulator, odor release apparatus, and taste delivery apparatus for visual, audio, tactile, odor and taste stimuli, respectively). The apparatus that delivers the stimuli is equipped, or integrated, with software to administer the delivery of the stimuli to the brain functional and physiological imaging apparatus. This software is also responsible to record the time and order of given stimuli. Once the brain multi-model imaging is completed and the brain feature activity data has been recorded, the organism is going through a labeling session. In this session, the stimuli are introduced again to the organism, so the organism can label the stimuli. Once completed, the raw data of the brain feature activity map and its labeling is analyzed, which utilizes a transformation that relates stimulus features to a pattern, or sequence of patterns, of brain activity using a functional encoding approach. As described, the Brain functional and physiological data is augmented with the Brain Regions and is then weighted according to the Brain Connectome to create the Activity Labels. To improve the specificity of the Activity Labels, the brain activity map is weighted by multiplying the brain activity map by the Brain Connectome matrices.

All of the above multi-modeling brain imaging technologies are components used to form a complex representation of the structure and functioning of the living brain. The combination of the multimodalities produces a multi-layer connectivity matrix. The combination of the Brain Regions Brain Connectome and Activity Labels are measured with at least two distinct method.

Stimuli content may represent a hard classification (e.g., a specific object, sound, tactile, odor, etc.) or a soft classification (subjective, individual-specific classification), such as emotional content, context, valence or arousal. The model uses the analyzed neuroimaging data to provide a set of regional brain responses through modeling such as general linear models or other approaches linked to specific classifications. An embodiment of the present invention relates to a sequence of brain feature activity maps, estimated from a video file or a sequence of images. The video is parcellated into a sequence of frames and each frame is deconstructed into its feature space to create the projected brain activity map. Then, a sequential brain activity map is composed to represent the dynamics of brain responses (e.g., create a video-specific brain response sequence as if the perception of the video was measured via a continuous brain activity measurement apparatus). During the creation of the projected brain activity maps, the labeling sequential brain activity map is given. The stimuli and labels are added together to form a sequential brain feature activity map database 144. Once created, a new sequence of images or a video file can be characterized based upon the match or a combination of designated matches of the sequential brain activity map database.

An embodiment of the present invention relates to a content contamination score (CCS). CCS is a measurable index that estimates the exposure levels for different content types by calculating the accumulated intensity of Activity Labels. When a new stimulus is presented, it converts into a projected brain activity map of Activity Labels and is labeled according to its content. CCS is a way to track the estimated exposure levels to harmful content and its potential effect by storing each Activity Label of each stimulus for each content class. By way of example, high CCS ranking for a given stimulus set of violent content could represent a high negative impact on the wellbeing of the potential viewer. The latter might label a stimulus set as 'not safe for work" (NSFW) or the viewer as in an impact zone (IZ). In the same manner, a low CCS ranking for a given stimulus set of violent content could represent low negative impact on the wellbeing of the potential viewer. The latter might label a stimulus set as 'safe for work" (SFW) or the viewer as in a safe zone (SZ).

An embodiment of the present invention relates to an enriched learning phase for modeling the brain feature activity map and database ("Enriched Learning Model"). During the Enriched Learning Model, a new stimulus is deconstructed into its feature space to create the projected brain activity map (i.e., create the image specific brain response as if the perception of the image was measured via a brain activity measurement apparatus). During the creation of the projected brain activity map, the labeling of the brain feature activity map is given (and not estimated). The stimuli labels are added to the existing brain feature activity map database 144 to create an enriched brain feature activity map database. After the enrichment learning phase, a new unlabeled stimulus can be characterized based upon the match or a combination of designated matches.

An embodiment of the present invention relates to a computer storage product with the computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hardwired circuitry in place of, or in combination with, machine-executable software instructions.

An embodiment of the present invention relates to a hardware circuit that can simulate the process of the brain feature activity map. The hardware is composed of multi-core hardware that can run at least 200 circuits simultaneously. Each circuit is physically connected through digital synaptic matrices to all other circuits in the apparatus, but communication between two circuits will occur according to the organism's Brain Connectome. Once a stimulus is presented to the hardware apparatus, a computer processor medium performs various computer-implemented operations to break down the feature of that given stimuli. The features are then transformed into another computer readable storage medium having computer code thereon for performing brain feature activity operations across the different hardware circuits.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A computer implemented method, comprising:
supplying stimuli to an organism;
labeling content of the stimuli that are applied to the organism;
measuring brain activity of the organism responsive to the stimuli;
producing a brain feature activity map characterizing the brain activity, by projecting the measured brain activity onto an anatomy-related space of the brain of the organism;
repeating the operations of supplying, measuring and producing for a plurality of stimuli while labeling the content of the stimuli based on a measured response of the organism to the stimuli to form an enriched brain feature activity map database including content labels;
receiving new stimuli;
mapping the new stimuli features to a projected brain activity map representing a projected response of the organism to the new stimuli;
comparing the projected brain activity map to the enriched brain feature activity map database to identify similarities and dissimilarities between the projected brain activity map of the organism and entries in the enriched brain feature activity map database to designate a match having a given content label associated therewith; and
generating an organism-specific characterization of the new stimuli by associating the given content label with the new stimuli;
generating a content contamination score (CCS) by scoring and ranking the organism-specific characterization of the new stimuli based on an impact on well-being of the organism;
outputting a first label in response to the organism-specific characterization of the new stimuli when the CCS is higher than a threshold; and
outputting a second label in response to the organism-specific characterization of the new stimuli when the CCS is lower than the threshold.

2. The method of claim 1 wherein the brain feature activity map includes brain connectivity matrices.

3. The method of claim 2 wherein the brain connectivity matrices include connectivity matrices weights based upon micro-structure estimates of brain tissue to form a Brain Connectome.

4. The method of claim 1 wherein the brain feature activity map is based upon cognitive layers combined with a connectivity association matrix.

5. The method of claim 1 wherein measuring is performed by one or more of Anatomical Magnetic Resonance Imaging (MRI), Diffusion Tensor Imaging (DTI), Functional MRI (fMRI), Electroencephalogram (EEG), Magnetoencephalogram (MEG), Infrared Imaging, Ultraviolet Imaging, Computed Tomography (CT), Brain Mapping Ultrasound, In-Vivo Cellular Data, In-Vivo Molecular data, genomic data, and optical imaging.

6. The method of claim 1 further comprising forming a hardware circuit corresponding to the brain activity map characterizing the brain activity, wherein the hardware circuit has active elements corresponding to the brain activity of the organism responsive to the stimuli.

7. The method of claim 1 further comprising:
supplying the stimuli to multiple organisms;
measuring the brain activity of the multiple organisms responsive to the stimuli;
producing brain feature activity maps characterizing the brain activity.

8. The method of claim 1 further comprising:
supplying additional labeled stimuli, wherein the additional labeled stimuli characterizes an anatomical response of the organism to the additional labeled stimuli; and
applying the additional labeled stimuli to the brain feature activity map to produce a new brain feature activity map.

9. The method of claim 8 wherein the additional labeled stimuli comprise a sequence of frames, images, sounds, tactile signals or odors that are projected to a sequence of new brain feature activity maps.

10. The method of claim 1 wherein the content labels include objectionable content labels and non-objectionable content labels.

11. The method of claim 10 wherein the objectionable content labels are based upon violent, sexual, abusive or offensive stimuli.

12. The method of claim 1 further comprising generating content guidelines based upon the brain feature activity map database.

13. The method of claim 1 wherein the content labels are used for a decision making process.

14. The method of claim 1 wherein producing the brain feature activity map comprises decomposing the stimuli into respective features in a feature space, such that the brain feature activity map characterizes the brain activity specific to the respective features, and wherein mapping the new stimuli features comprises deconstructing the new stimuli into the feature space and modeling the features of the deconstructed new stimuli to create the projected brain activity map.

15. The method of claim 14 wherein modeling the features comprises transforming the features of an image to brain activity using a functional encoding approach.

* * * * *